US006368990B1

(12) United States Patent
Jennergren et al.

(10) Patent No.: US 6,368,990 B1
(45) Date of Patent: *Apr. 9, 2002

(54) FABRICS FORMED OF HOLLOW FILAMENTS AND FIBERS AND METHODS OF MAKING THE SAME

(75) Inventors: Bengt Jennergren, Norrköping; Peter Nikko, Aby; Urban Lindberg, Gusum; Hakan Holmer, Asensbruk, all of (SE)

(73) Assignee: BBA Nonwovens Sweden AB (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/122,564

(22) Filed: Jul. 24, 1998

Related U.S. Application Data

(60) Provisional application No. 60/054,727, filed on Aug. 5, 1997.

(51) Int. Cl.[7] .............................. D04H 1/00; D04H 3/00
(52) U.S. Cl. ..................... 442/329; 442/338; 442/350; 442/361; 442/401; 442/329; 442/194
(58) Field of Search ................................ 442/338, 350, 442/361, 401, 409, 329, 194

(56) References Cited

U.S. PATENT DOCUMENTS

| 4,699,619 A | 10/1987 | Bernardin |
| 4,874,666 A | * 10/1989 | Kubo et al. ................ 428/398 |
| 5,068,141 A | 11/1991 | Kubo et al. |
| 5,188,625 A | 2/1993 | Van Iten et al. |
| 5,622,671 A | 4/1997 | Pellegrin et al. |

FOREIGN PATENT DOCUMENTS

| EP | 0 277 707 A2 | 8/1988 |
| EP | 0 277 707 A | 8/1988 |
| EP | 0 462 574 A | 12/1991 |
| EP | 0 596 532 A | 5/1994 |
| GB | 2 041 821 A | 8/1980 |

OTHER PUBLICATIONS

Database WPI, Section Ch, Week 9151 Derwent Publications Ltd., London, GB; Class A17, An 91–372421 XP002108683 & JP 03 249254 A (UnitikaLtd), Nov. 7, 1991—Abstract.

Database WPI, Section Ch, Week 8930 Derwent Publications Ltd., London, GB; Class A96, AN 89–217676 XP002108684 & JP 01 156563 A (Toyobo KK), Jun. 20, 1989—Abstract.

Patent Absracts of Japan vol. 017, No. 037 (C–1019), Jan. 25, 1993 & JP 04 253857 A (Oji Paper CLtd), Sep. 9, 1992—Abstract.

* cited by examiner

*Primary Examiner*—N. Edwards
(74) *Attorney, Agent, or Firm*—Alston & Bird LLP

(57) ABSTRACT

The present invention provides nonwoven fabrics formed of hollow filaments and/or hollow staple fibers and processes for producing the same. The hollow spunbonded filaments and hollow staple fibers are formed of a polypropylene composition. The resultant fabrics of the invention can be useful in numerous applications, such as components of medical garments and disposable absorbent products.

31 Claims, 15 Drawing Sheets

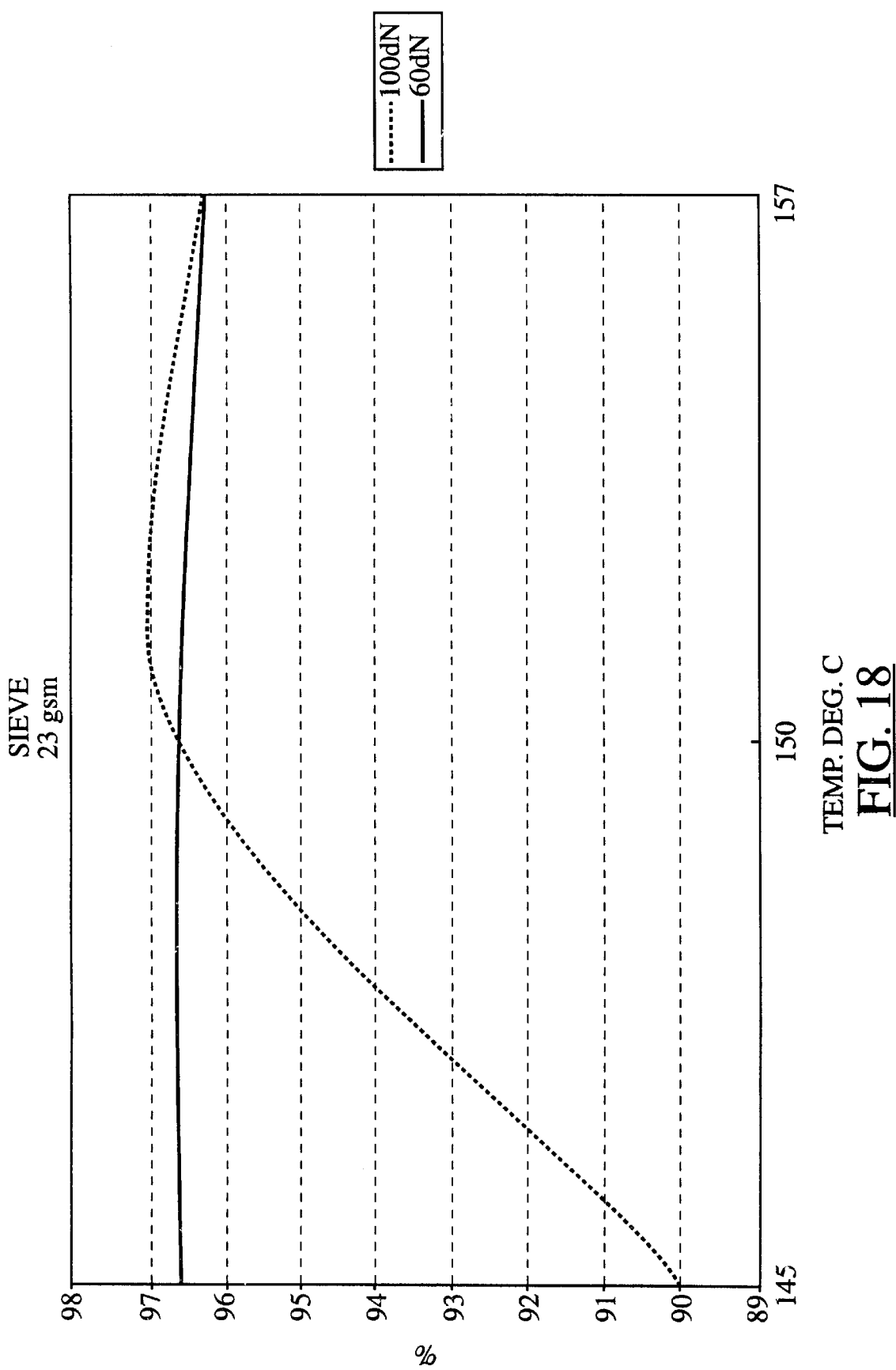

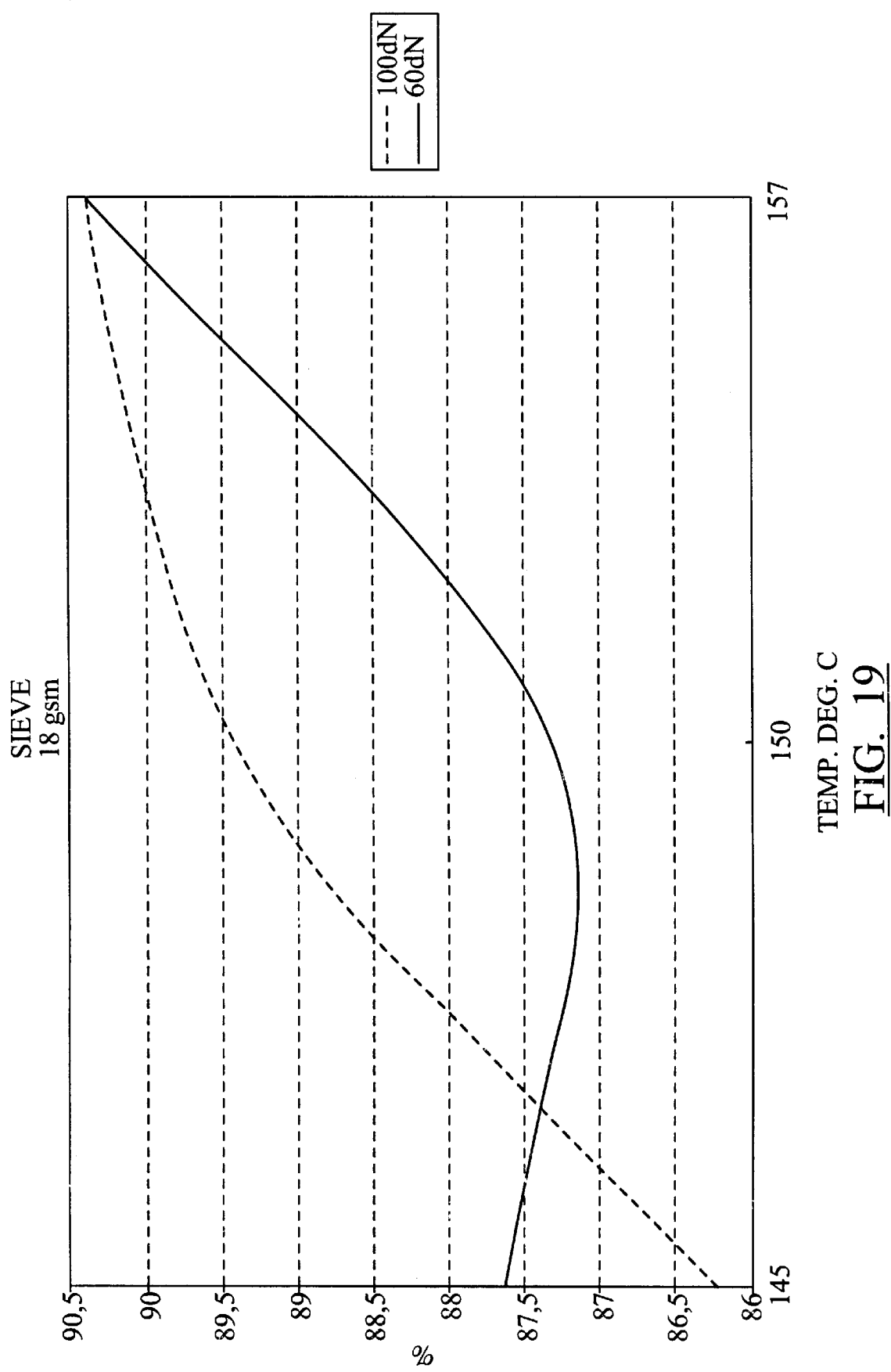

FABRICS FORMED OF HOLLOW FILAMENTS AND FIBERS AND METHODS OF MAKING THE SAME

CROSS-REFERENCE TO RELATED APPLICATION

This application is related to Provisional Application Ser. No. 60/054,727, filed Aug. 5, 1997, and claims the benefit of its filing date under 35 USC §119(e).

FIELD OF THE INVENTION

The invention relates to nonwoven fabrics and to processes for producing nonwoven fabrics. More specifically, the invention relates to nonwoven fabrics formed of hollow filaments and/or hollow fibers, useful for hygiene, medical, and industrial applications.

BACKGROUND OF THE INVENTION

Nonwoven fabrics are widely used as components of nonwoven laminates for a variety of specific end uses. Nonwoven fabric laminates can be used in hygiene applications, such as disposable diapers, feminine hygiene products, incontinence pads, and the like; in medical applications, such as in disposable medical garments; and the like.

For example, disposable hygiene products, such as disposable diapers, typically include a liquid impermeable outer covering, an absorbent layer, and an inner layer which contacts the skin of the wearer. The liner layer can be a liquid permeable, porous nonwoven fabric, such as a carded web or a spunbonded web, and the outer covering can include a spunbonded or carded nonwoven fabric treated to impart barrier properties thereto, for example, by laminating the fabric to a polyolefin film.

A primary function of hygiene products is to contain body exudates to prevent soiling, wetting, or contamination of clothing or other articles. Hygiene products are also constructed to rapidly absorb waste, ideally permitting liquid to flow rapidly through the layer adjacent the wearer into the absorbent layer without permitting or facilitating re-transmission of liquid from the absorbent layer to the wearer side of the inner layer.

Other useful nonwoven laminate articles include barrier fabric which include one or more microfibrous layers, such as meltblown webs, sandwiched between outer spunbonded webs of continuous filaments. The barrier meltblown webs impede the passage of bacteria and other contaminants, and the outer spunbonded webs reinforce the inner webs and provide abrasion resistance.

Issues associated with the use of nonwoven fabrics in laminate applications include the ability of the laminate to contain waste, facilitate liquid strikethrough and minimize rewet, and provide barrier properties. This can be particularly problematic in hygiene products due to decreasing basis weights of nonwoven components to meet the increasing demands for thinner products.

Another issue in nonwoven laminate fabrics is the ability to provide the combination of contradictory properties, such as pleasing aesthetics (softness, flexibility, and the like) and strength and abrasion resistance in a single fabric. For example, spunbonded webs used in laminate products are typically formed of 100% polypropylene filaments to reinforce and protect inner layers from excessive stresses and potential damage during use. The resultant laminate can be more durable and have an improved appearance. This can also minimize contamination of sterile surfaces in medical applications by preventing loose fibers from contaminating sterile environments. However, polypropylene fabrics can suffer from poor aesthetics.

Fibrous webs formed of polyethylene can exhibit improved aesthetics relative to polypropylene fabrics, which make them desirable for incorporation into composite nonwoven fabrics. Nonetheless, in spite of these advantages, such fabrics suffer poor abrasion resistance, resulting in an unsightly fuzzed appearance and possible contamination in sterile environments.

SUMMARY OF THE INVENTION

The present invention provides nonwoven fabrics which can exhibit a combination of various properties, such as improved barrier and containment, good abrasion resistance and tensile strength, pleasing aesthetics, and the like. In one embodiment of the invention, the fabrics include a plurality of hollow continuous spunbonded filaments. In another embodiment of the invention, the fabrics include a plurality of hollow staple fibers. The hollow filaments and the hollow staple fibers are formed of a polypropylene composition. Exemplary polypropylene compositions include 100% polypropylene compositions and blends of polypropylene as the dominant or majority component with at least one other polymer.

The hollow spunbonded filaments and hollow staple fibers can impart several advantageous properties to the fabrics. For example, the use of hollow filaments and/or hollow staple fibers can allow the fabric manufacturer to increase the number of filaments and/or fibers in a fabric for a given basis weight, or conversely, to lower the basis weight of a fabric without lowering the number of filaments and/or fibers. This can improve the barrier properties of the fabrics without unduly increasing basis weight. This can also improve resistance to bleed through of adhesives and improved SAP containment and strikethrough/rewet for hygiene applications, due to the increased number of filaments and/or fibers for a given basis weight. The fabrics of the invention can also exhibit improved abrasion and similar or improved tensile and tear properties, as compared to heavier basis fabrics formed of solid filaments and/or fibers. Still further, the fabrics of the invention can exhibit improved (higher) opacity as compared to fabrics formed of solid filaments.

The fabrics can also exhibit abrasion resistance. This can increase durability and improve the appearance of disposable hygiene and other products. This can also minimize or prevent contamination of sterile environments due to loose fibers abraded from the surface of a nonwoven article in medical applications.

It is also currently believed that the hollow filaments and fibers can improve bonding properties of the fabrics. For example, it is believed that the fabrics of the invention can be thermally bonded to provide a cohesive fabric using lower bonding temperatures and/or a wider bonding window (i.e., wider range of bonding conditions). As a result, fabrics can be produced more readily which have superior strength and abrasion resistance.

For example, when comparing fabrics formed of solid fibers with the fabrics of the invention which include hollow fibers at a constant number of fibers per unit area and constant outer fiber diameter, the amount of material that has to be softened or melted to form the bonding points will be less for the hollow fibers. Thus, in a calender bonding process in which calender rolls are used to bond the nonwoven, the energy and pressure needed to compress and melt the bonding points will be less when hollow fibers are used. On the other hand, a nonwoven fabric which includes hollow fibers will have more fibers per unit area, as compared to a nonwoven fabric formed of solid fibers, at the same basis weight and with the same outer diameter of the fibers. This can give a stronger bonded material because more fibers can be tied down in the bonding points or sites.

Still further, the fabrics of the invention can exhibit desirable volumetric capacity. The volumetric capacity of a fabric can be defined as the portion of the total fabric volume not occupied by fibers and binders. Volumetric capacity can be important for storing, suspending or transporting other materials (gas, liquid or solid) by a nonwoven fabric. Fabrics made from hollow fibers can exhibit a higher volumetric capacity per unit of fabric weight and hence can be more efficient than conventional carrier fabrics made from solid fibers formed of the same material. For a typical thermally bonded nonwoven fabric, the ratio of volumetric capacity, $V_c$, to fabric mass, $M_{nw}$, can be expressed as:

$$V_c/M_{nw} = (t/Bwt) - (1/\rho)$$

wherein t=fabric thickness; Bwt=fabric basis weight; and $\rho$=density of fiber polymer type. Thus, for the ratio of void volume to fabric weight to increase for a given fabric construction, one must reduce basis weight while not effecting the fabric construction or geometry. The fabrics of the invention which include hollow fibers or filaments can achieve this improvement. Although the foregoing example applies to a homogenous, fibrous nonwoven fabric, the equation can be easily modified to include multi-component fibers as well as adhesive binders. Still further, the fabrics can exhibit improved (increased) capacity.

The hollow filaments and/or fibers are also believed to form stronger thermal bonds (in the fabric and in laminate structures) than comparable solid filaments and fibers. The thermal bonds can also have greater bond area relative to thermal bonds formed of comparable solid filaments or fibers. This can also improve fabric strength and abrasion resistance.

Further, by using hollow fibers, it is possible to increase the number of fibers for a given basis weight without sacrificing the loft of the nonwoven, due to the constant outer diameter of the hollow fibers or filaments. That is, with solid fibers, one can normally only increase the number of fibers for a given basis weight by reducing fiber outer diameter. However, decreased fiber diameter can result in reduced loft. The loft of a fabric can be important with regard to both aesthetic and physical properties of the fabric.

BRIEF DESCRIPTION OF THE DRAWINGS

Some of features and advantages of the invention having been stated, others will become apparent from the detailed description which follows, and the accompanying drawings which form a part of the original disclosure of this invention, and in which:

FIGS. 18 and 19 are graphs illustrating the influence of bonding temperature and pressure on the permeability of exemplary fabrics of the invention.

DETAILED DESCRIPTION OF THE INVENTION

The present invention will now be described more fully hereinafter with reference to the accompanying drawings, in which illustrative embodiments of the invention are shown. This invention may, however, be embodied in many different forms and should not be construed as limited to the embodiments set forth herein. Rather, this embodiment is provided so that the disclosure will be thorough and complete, and will fully convey the scope of the invention to those skilled in the art. Like numbers refer to like elements throughout. For purposes of clarity, the scale has been exaggerated.

Figure 1:
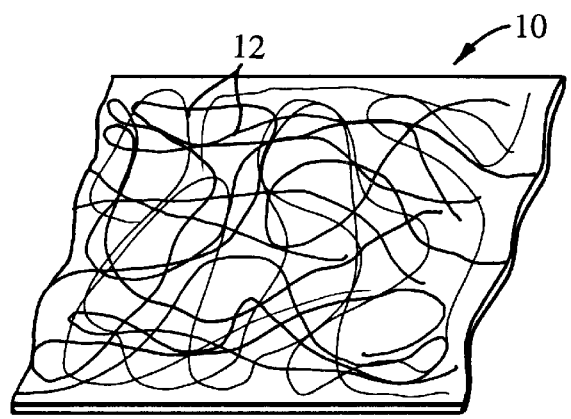
FIG. 1 is a fragmentary top view of a fabric of hollow spunbonded filaments in accordance with one embodiment of the present invention.
Figure 2:
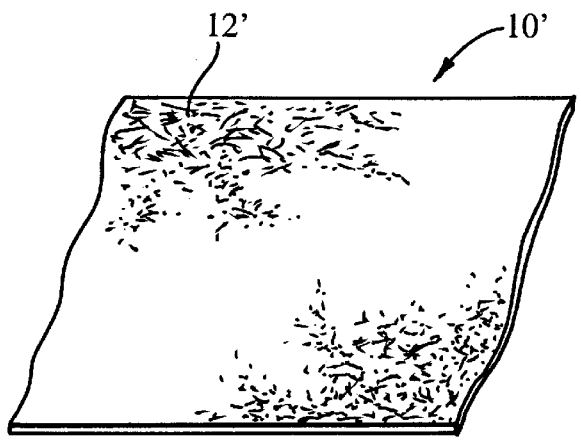
FIG. 2 is a fragmentary top view of a fabric of hollow staple fibers in accordance with another embodiment of the present invention.

FIG. 1 is a fragmentary top view of one embodiment of the invention, namely a spunbonded fabric designated generally as 10, which includes a plurality of hollow continuous spunbonded filaments 12. FIG. 2 is a fragmentary top view of another embodiment of the invention, namely fabric 10', which includes a plurality of hollow staple fibers 12'. Both fabric 10 and fabric 10' can have a basis weight in the range of about 5 to about 500 grams per square meter (gsm). The fabrics may be used alone or as a component of various articles or garments such as disposable hygiene products, including disposable diapers, incontinence briefs, feminine hygiene products, and the like; medical products, including sterile wraps, surgical gowns, surgical drapes and the like; industrial garments; filtration media; agricultural products; disposable wipes; and the like.

Preferably, the fabrics of the invention include spunbonded filaments and/or staple fibers having a degree of hollowness ranging from about 5% to about 70%, and more preferably about 10 to about 50%. The percentage of hollowness of the hollow spunbonded filaments and hollow staple fibers is determined by factors like the polymer or polymers used, the melt temperature, the quenching of the filaments, the spinning speed, output/spinnerettes hole and the spinneret design.

Figure 6A:
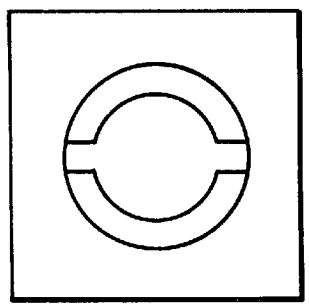
FIGS. 6a, 6b, and 6c are enlarged cross sectional views of a portion of a spinneret of FIG. 5.
Figure 6B:
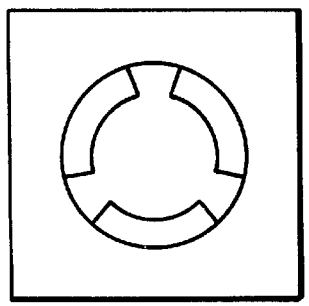
Figure 6C:
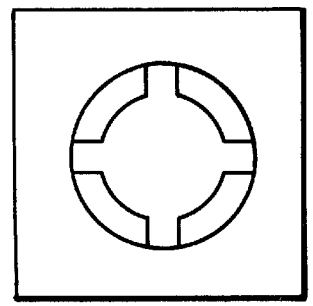

Useful spinnerettes for solid fibers are known to those skilled in the art. In order to be able to produce hollow fibers, the typical spinneret design for solid fibers can be used but with a modified orifice. The orifice can be of different designs, such as 2C, 3C, or 4C configurations (for example, as illustrated in FIGS. 6a–6c and discussed below).

The percentage of hollowness of the hollow spunbonded filaments and hollow staple fibers can be determined in different ways. In one exemplary technique, one cuts the fibers and measures the area of the hollowness and the cross area of the fibers. The ratio of the two areas gives the percentage hollowness. The measurement can be made in a light microscope or a SEM (scanning electron microscope). Another exemplary technique is to measure the diameters of the fibers and the hollowness from the side of the fiber. This can give a higher standard deviation especially when the hollowness is not perfectly round. These and other techniques are known ion the art.

The hollow spunbonded filaments and hollow staple fibers can be hollow along a substantial portion of the length of the filament or fiber (i.e., greater than 75% of the length thereof). Hollow spunbonded filaments and hollow staple fibers can also have both hollow and solid portions along the length thereof. The shape of the inner diameter of the hollow continuous filaments and hollow staple fibers can be substantially circular or can be a modified shape (such as triangular). The fabrics of the invention can include other fibers and/or filaments, including solid spunbonded filaments and/or solid staple fibers, so long as the fabric includes at least about 50% by weight hollow spunbonded filaments or hollow staple fibers.

Hollow filaments 12 of fabric 10 and hollow staple fibers 12' of fabric 10' are formed of a polypropylene composition. The polypropylene can be 100% polypropylene. The polypropylene composition alternatively can be a blend of at least two components, a polypropylene component as a dominant portion of the blend and at least one other polymer as the minority component. A preferred minority component is polyethylene, which is immiscible with polypropylene and which forms a distinct, separate phase in the filaments.

When a blend is used, the continuous filaments comprise about 99 to about 50 percent by weight polypropylene, and about 1 to about 50 percent by weight of at least one other polymer. A preferred composition includes about 80 to about 98 percent by weight polypropylene and about 2 to about 20 percent by weight polyethylene. Blend compositions which include polyethylene can be especially suited for applications requiring good extensibility, as well as good tensile strength and abrasion resistance.

Various polypropylene polymers known to the skilled artisan can be used in the invention. In general, the polypropylene component can be an isotactic or syndiotactic polypropylene homopolymer, copolymer, or terpolymer with the most preferred being in the form of a homopolymer. Exemplary commercially available polypropylene polymers useful in the present invention include, but are not limited to, isotactic polypropylene commercially available as the Moplen series from Montel, isotactic polypropylene commercially available from Borealis and Exxon, and the like.

Various types of polyethylene are useful as the minority component of the blend, including low density polyethylene, high density polyethylene and linear low density polyethylene (LLDPE), produced from any of the well known processes, including, without limitation, Ziegler-Natta catalyst processes, single site or metallocene catalyst processes, and the like. Exemplary polyethylene polymers include low density polyethylene (LDPE) commercially available from Borealis and Exxon, the Exact Series of polymers commercially available from the Exxon Chemical Company, and the Affinity polymers available from the Dow Chemical Company.

Other polymers can also be utilized as minority components in the blend. Preferably, such polymers are soft and elongatable, such as the Catalloy polyolefins (co- and ter-polymers of propylene) available from Himont Incorporated.

Blends with more than two polymers may also be utilized, including those with three and four polymer components. Additional polymers may be added to a two component blend to impart additional properties or benefits with respect to blend compatibility, viscosity, polymer crystallinity, phase domain size, and the like. Other additives conventionally used in the production of polymer filaments and fibers can also be incorporated in the polymer, such as but not limited to, UV stabilizers, pigments, delusterants, lubricants, antistatic agents, water and alcohol repellents, etc., in conventional amounts, which are typically no more than about 10% by weight.

Figure 3:
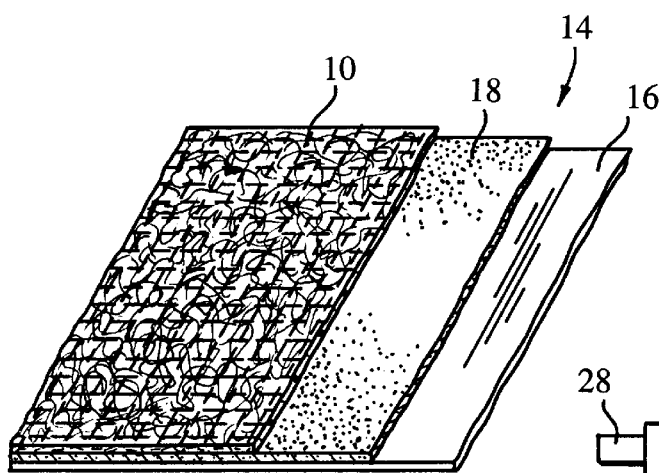
FIG. 3 is a fragmentary top view of an illustrative laminate fabric of the present invention with the respective layers of the fabric being exposed for clarity of illustration.

The fabrics of the invention can be formed and/or laminated to at least one other component to form a composite nonwoven fabric. An exemplary nonwoven fabric laminate 14 is illustrated in FIG. 3. As shown, the laminate fabric 14 includes first and second outer nonwoven webs 10 and 16. Sandwiched between and laminated to the outer nonwoven webs 10 and 16 is one or more additional layers or webs 18. For the purposes of the invention, at least one of the outer webs (10 for example) is formed of a plurality of hollow filaments as described above. Although fabric 10 is illustrated in FIG. 3, the skilled artisan will appreciate that fabric 10' can also be used in combination with other layers or webs, and further that one or more fabrics 10 and 10' can be used in combination together and with additional webs.

The other webs 16 and 18 can be any of a variety of structures which are well known to those skilled in the art and may be formed from any of the known and suitable polymers. For example, web 16 and/or 18 can be a staple nonwoven web, a spunbonded nonwoven web, a meltblown nonwoven web, a film or a mat. In addition, web 16 and/or 18 optionally can include hollow continuous filaments similar to those of the first outer nonwoven web 10 and/or hollow staple fibers. Although a trilaminate composite laminate fabric 14 is illustrated in FIG. 3 having two outer webs 10 and 16 and a single central layer or web 18, other combinations of webs can form a laminate fabric within the scope of the invention.

Figure 4:
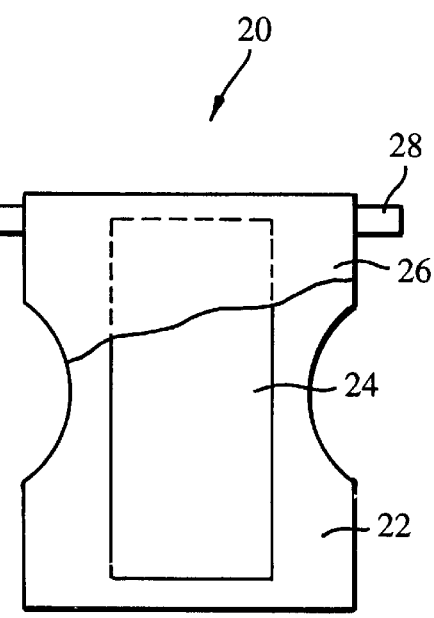
FIG. 4 is a fragmentary top plan view of an illustrative absorbent article incorporating a nonwoven fabric in accordance with the invention.

The fabrics of the invention can also be used as components of other nonwoven fabric laminate structures as known in the art. For example, fabrics formed of hollow spunbonded filaments and/or hollow staple fibers are useful as components in disposable hygiene products, such as coverstock (topsheet, backsheet), leg cuffs, etc. in disposable diapers. FIG. 4 illustrates a fragmentary top plan view of a disposable diaper, designated generally at 20. Disposable diaper 20 includes a substantially liquid impermeable backsheet layer 22, an absorbent layer 24 positioned on backsheet layer 22, and a liquid permeable topsheet layer 26 positioned on absorbent layer 24. Diaper 20 also can include a liquid acquisition and transport layer as known in the art disposed between absorbent layer 24 and topsheet layer 26.

Backsheet layer 22 and topsheet layer 26 are essentially coextensive and extend out past the edges of absorbent layer 24 to form marginal edges about the periphery of diaper 20. Diaper 20 is illustrated as having a general hourglass or I-shape, but as will be appreciated by the skilled artisan, other product shapes may be used, depending upon the desired properties and end use of the product. Diaper 20 can also include fasteners 28 for fastening the diaper on the wearer. As illustrated, fasteners 28 are adhesive tape tabs; however, any of the fasteners known in the art, such as hooks, clips, snaps, hook and loop types fastener systems such as Velcro and the like, may be used.

Backsheet layer 22 and/or topsheet layer 26 can include as a component a fabric of the invention which includes hollow spunbonded filaments and/or hollow staple fibers. When incorporated as a component of backsheet 22, preferably the fabrics of the invention are combined with a suitable liquid impermeable layer, such as a polyolefin film. Backsheet layer 22 and/or topsheet layer 26 can also include other conventional nonwoven fabrics. The fabrics of the invention can also be incorporated into leg flaps, barrier leg cuffs, and the waistband of the absorbent personal care product to improve containment and prevent leakage.

Figure 5:
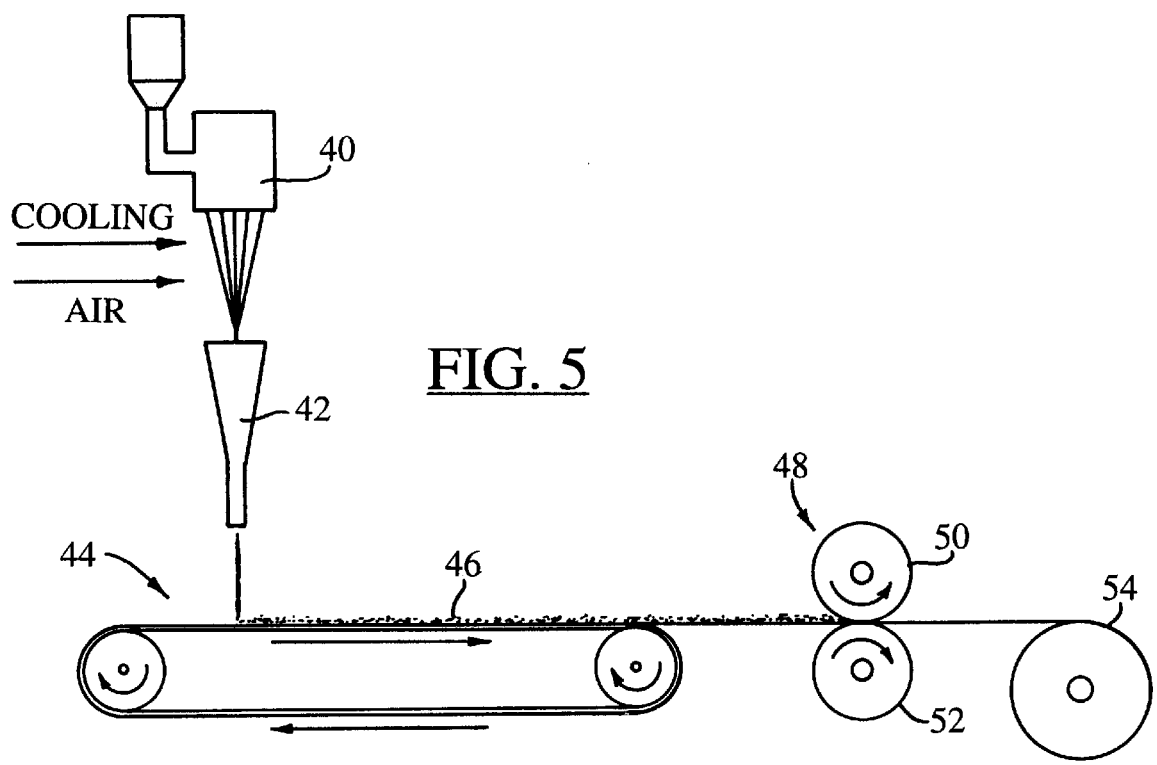
FIG. 5 is a schematic side view of an illustrative process in accordance with the present invention for forming the fabric of FIG. 1.

Turning now to FIG. 5, a schematic side view of an illustrative process for forming the fabrics which include hollow spunbonded filaments of the invention is illustrated. In producing filaments formed of a blend, the polymer components of the blend can be combined in appropriate proportional amounts and intimately blended before being melt-spun. In some cases sufficient mixing of the polymer components can be achieved in the extruder as the polymers are converted to the molten state, although it may be preferable to use a separate mixing step. Among the commercially well suited mixers that can be used include the Barmag 3DD three-dimensional dynamic mixer supplied by Barmag AG of Germany and the RAPRA CTM cavity-transfer mixer supplied by the Rubber and Plastics Research Association of Great Britain.

Referring again to FIG. 5, a continuous filament web is formed by extruding a polymer composition through a generally linear die head or spinneret 40 for melt spinning substantially continuous filaments. The spinneret preferably produces the filaments in substantially equally spaced arrays. To provide hollow filaments, conventional circular die orifices can be modified, for example, to provide a 2C, 3C or 4C configuration, such as illustrated in FIGS. 6a, 6b, and 6c, respectively. In the design of the orifice, it can be important to consider the Barus effect (swell of the polymer when it leaves the orifice). If the Barus effect is high, then the diameter of the C's should be high to maximize percentage hollowness. The distance between the end of the C's can also be higher as the melt from the different C's can flow together. It is also important to consider the area of the C's through which the melt flows to provide a comparable pressure in the spinnerettes as for solid fibers.

The substantially continuous filaments are extruded from the spinneret and quenched by a supply of cooling air. The filaments are directed to an attenuator 42 after they are quenched, and a supply of attenuation fluid, typically air, is admitted therein. Although separate quench and attenuation zones can be used, it will be apparent to the skilled artisan that the filaments can exit the spinneret directly into the attenuator where the filaments can be quenched, either by the supply of attenuation air or by a separate supply of quench air. Fiber attenuation can also be achieved using rolls (roll drawing) in addition to pneumatic drawing.

The attenuation air may be directed into the attenuator by an air supply above the entrance end, by a vacuum located below a forming wire or by the use of eductors integrally formed in the attenuator. The air proceeds down the attenuator, which narrows in width in the direction away from the spinneret, creating a venturi effect and causing filament attenuation and drawing. The attenuator used in the spunbonding process may be of any suitable type known in the art, such as a slot draw apparatus or a tube-type (Lurgi) apparatus. The air and filaments exit the attenuator, and the filaments are collected on a collection surface 44 as a continuous filament web 46.

The continuous filament web 46 is then longitudinally directed to a thermal treatment station 48 comprising cooperating calender rolls 50, 52 to form a multiplicity of thermal point bonds to provide a coherent nonwoven fabric. Bonding conditions, including the temperature and pressure of the bonding rolls, vary according to the particular polymers used, and are known in the art for differing polymers. For example, for a 100% polypropylene with a melt flow rate (MFR) of about 35, the bonding temperature can be about 130° C. to about 170° C. and bonding pressure about 40–120 decaNewton (dN).

Although bonding rolls are illustrated in FIG. 5, other thermal treating stations such as ultrasonic, microwave or other RF treatment zones which are capable of bonding the fabric can be substituted for the bonding rolls of FIG. 5. Such conventional heating stations are known to those skilled in the art and are capable of effecting substantial thermal fusion of the nonwoven webs. In addition, other bonding techniques known in the art can be used, such as by hydroentanglement of the fibers, needling, and the like. It is also possible to achieve bonding through the use of an appropriate bonding agent as known in the art. Autogenous bonding can also be used, in which filaments are contacted with a gas which will render the filaments cohesive and form bonds at their contacting points. For example, the surface of the filaments may be activated chemically by providing an acid gas (such as hydrochloric acid) and steam mixture, or activated thermally by providing steam heated to a temperature at which the surface of the filaments are activated to achieve bonding. Through air bonding may also be used, optionally with the use of a binder fiber. Any pattern known in the art may be used with typical embodiments employing continuous or discontinuous patterns.

The spunbonded fabric can then be removed from the assembly and stored on a roll 54, or alternatively, passed on to additional manufacturing processes.

Figure 7:
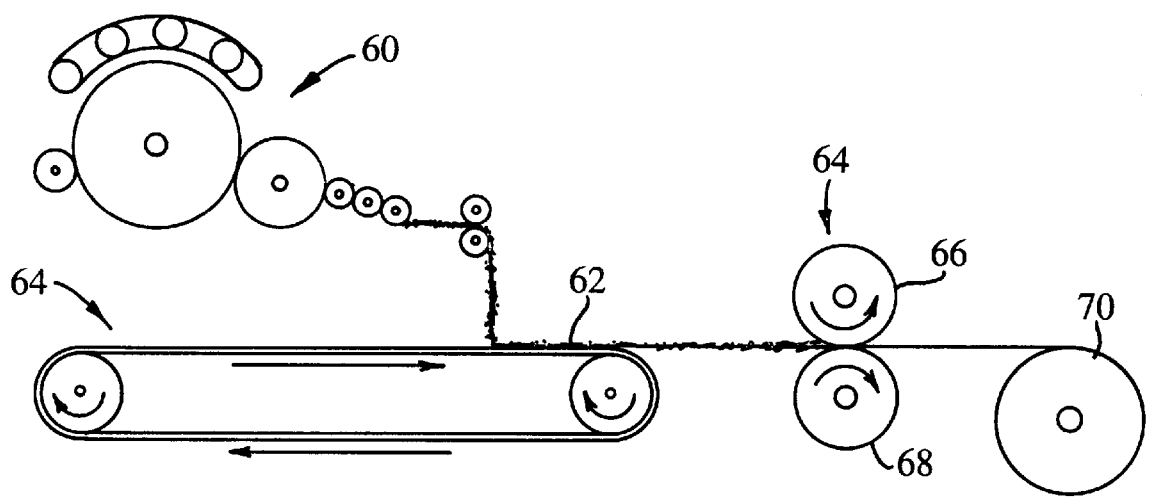
FIG. 7 is a schematic side view of an illustrative process in accordance with the present invention for forming the fabric of FIG. 2.
Figure 8:
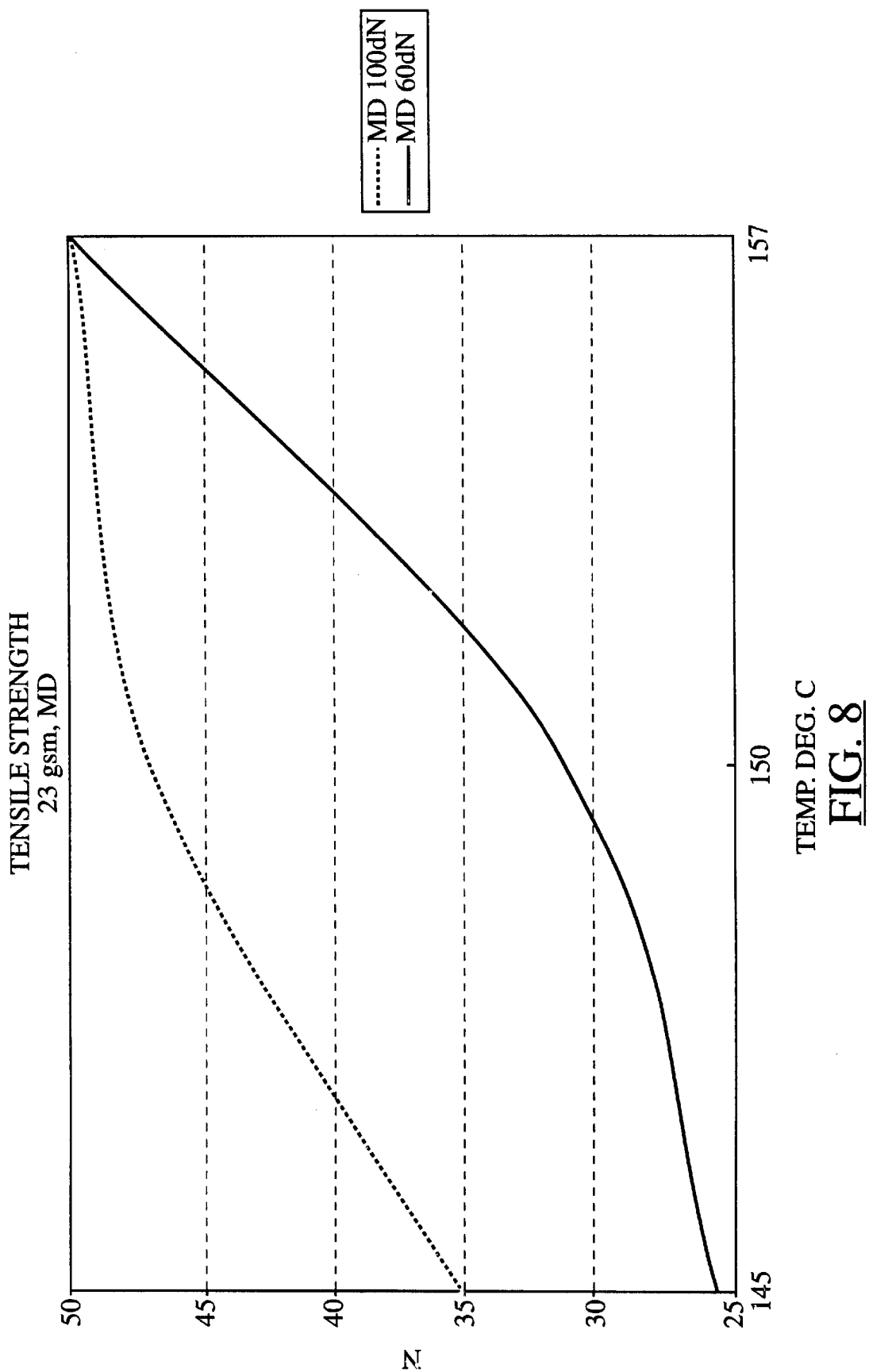
FIGS. 8–11 are graphs illustrating the influence of bonding temperature and pressure on tensile strength of exemplary fabrics of the invention.
Figure 9:
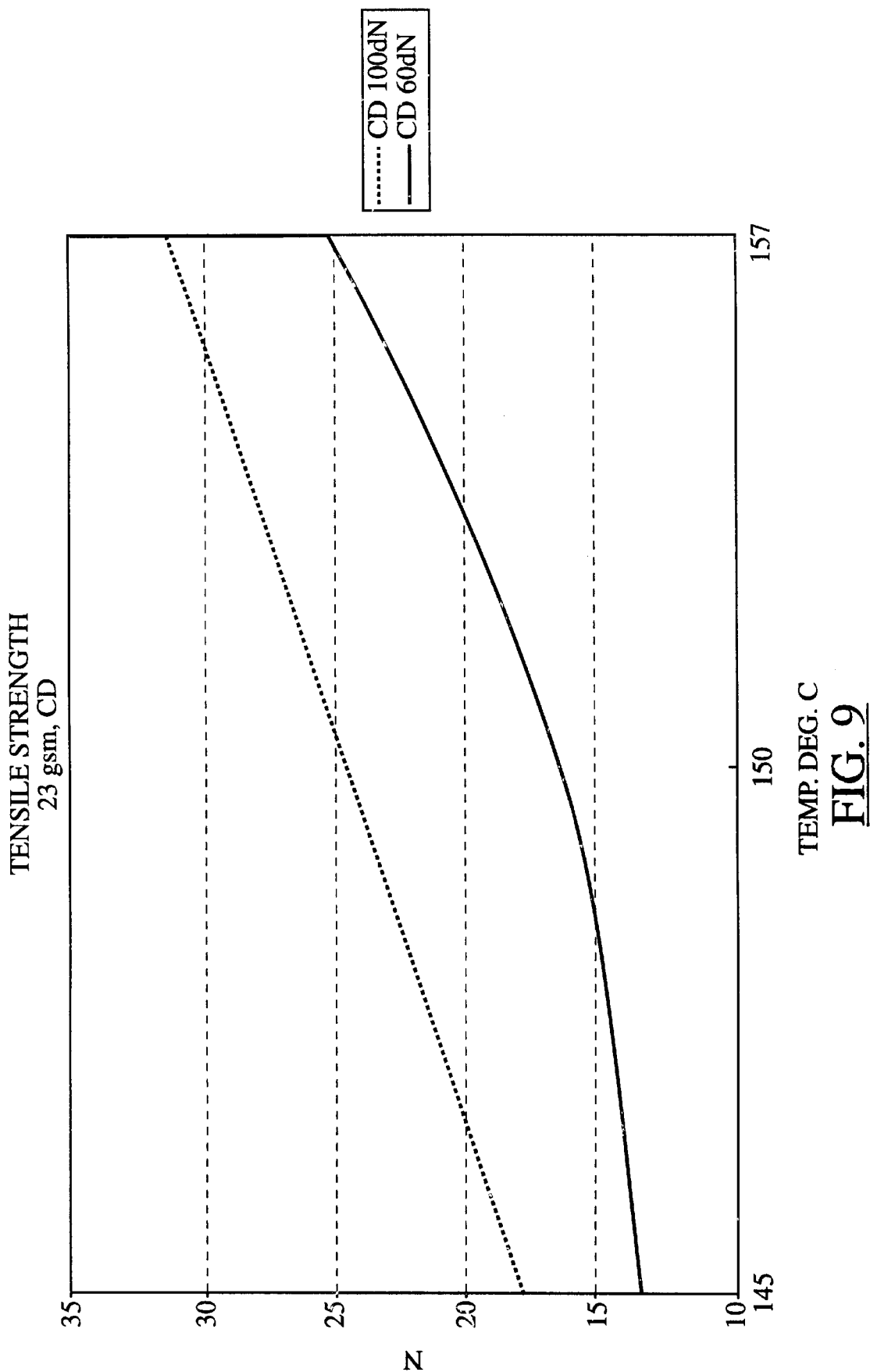
Figure 10:
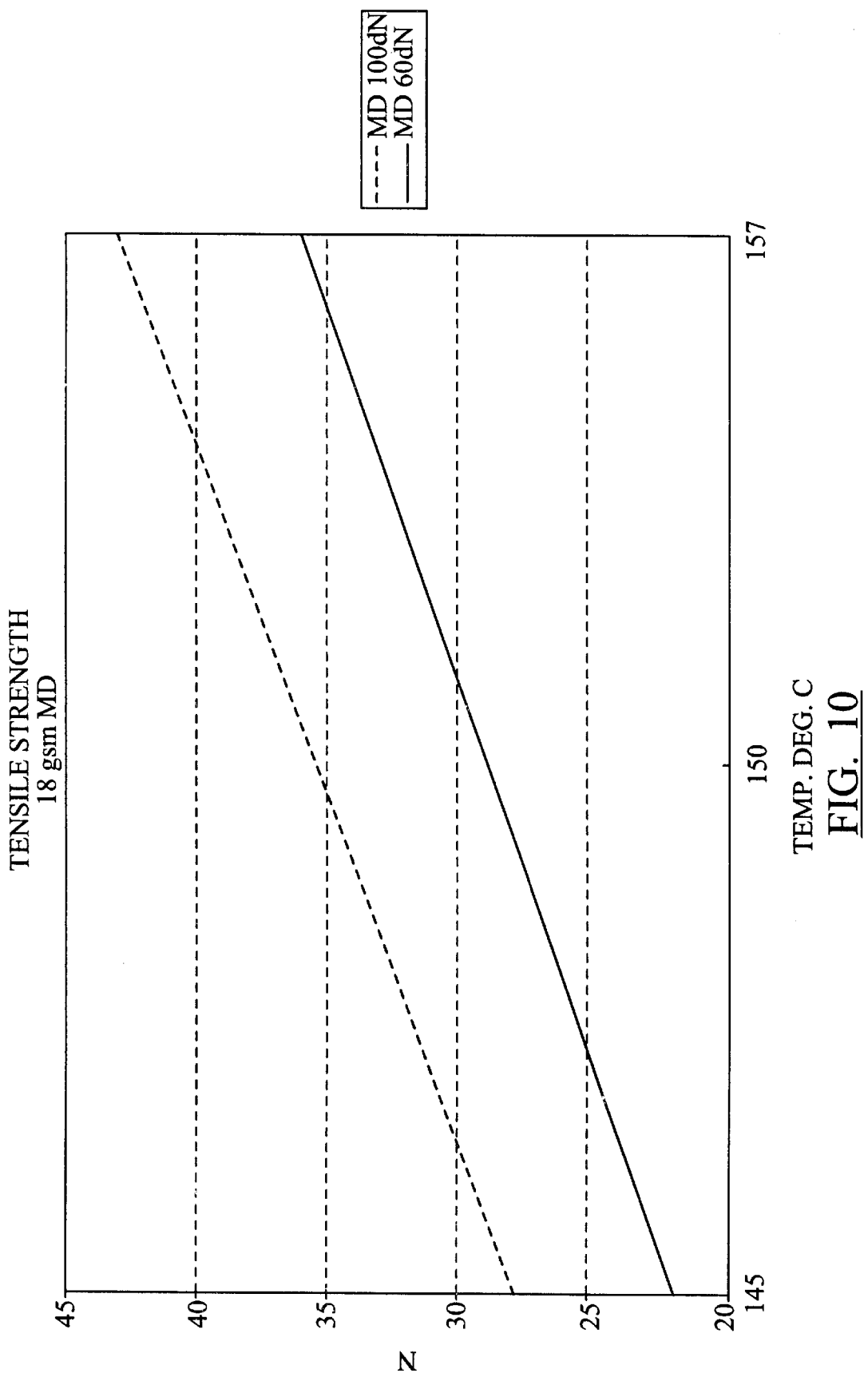
Figure 11:
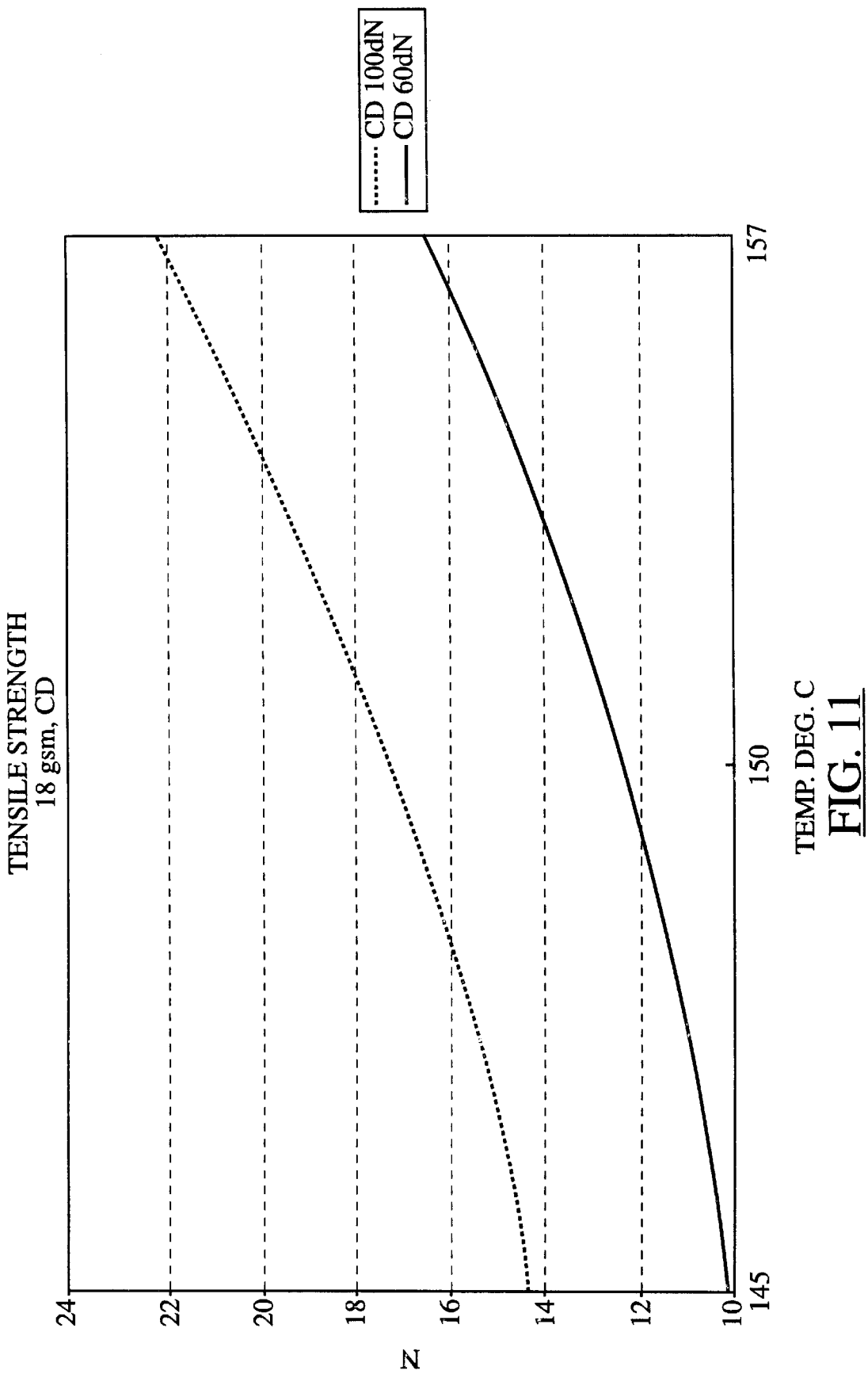
Figure 12:
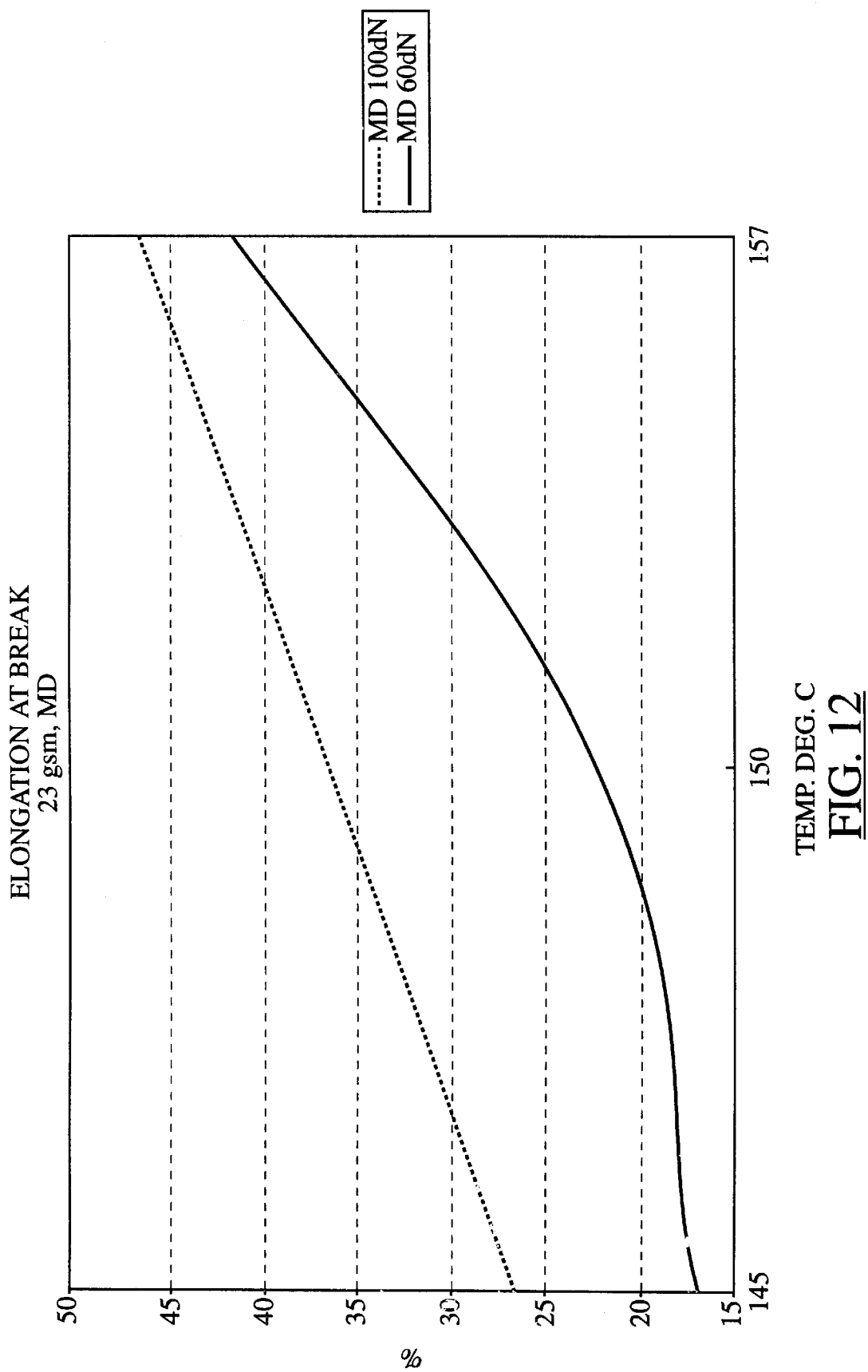
FIGS. 12–15 are graphs illustrating the influence of bonding temperature and pressure on elongation at break of exemplary fabrics of the invention.
Figure 13:
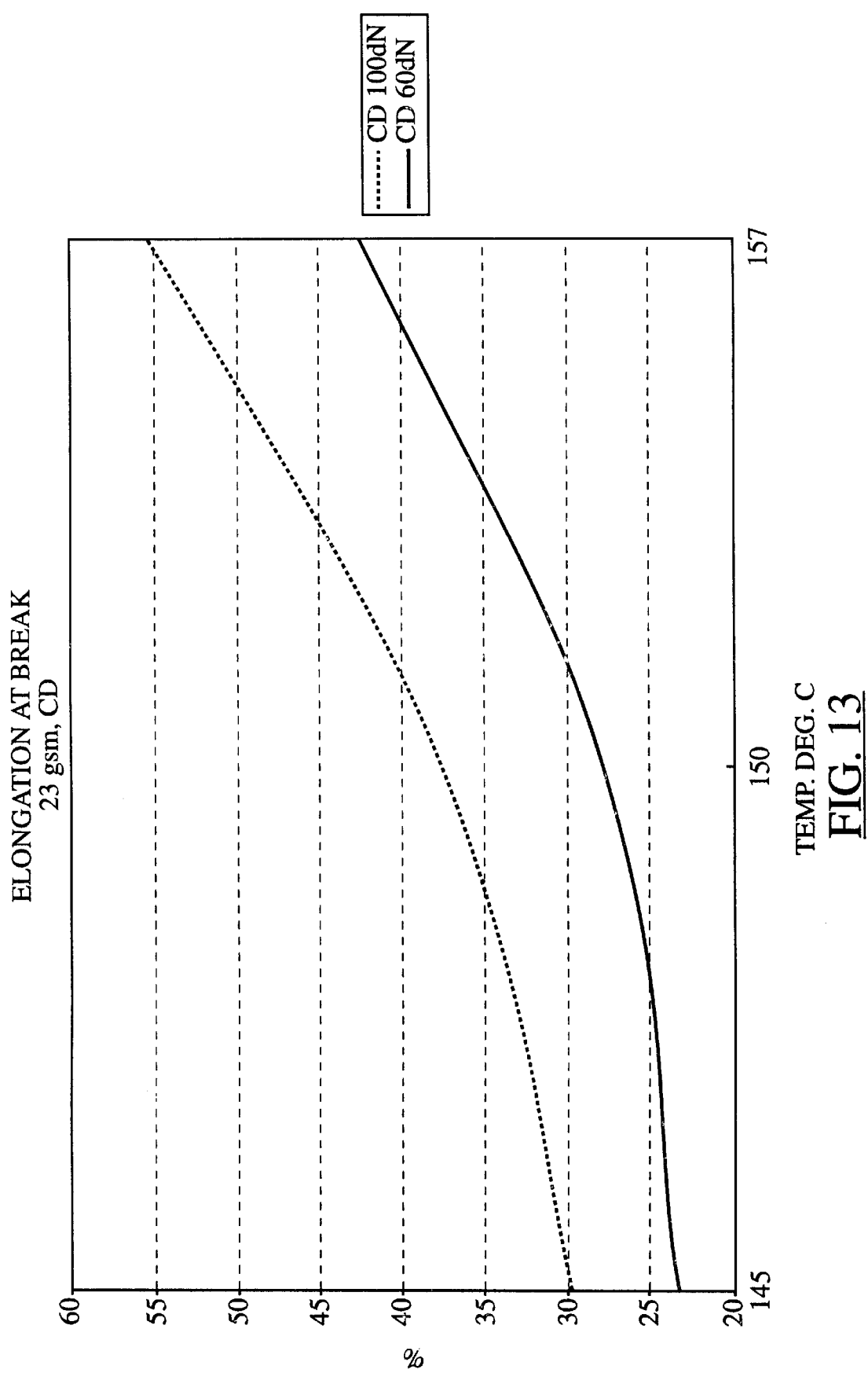
Figure 14:
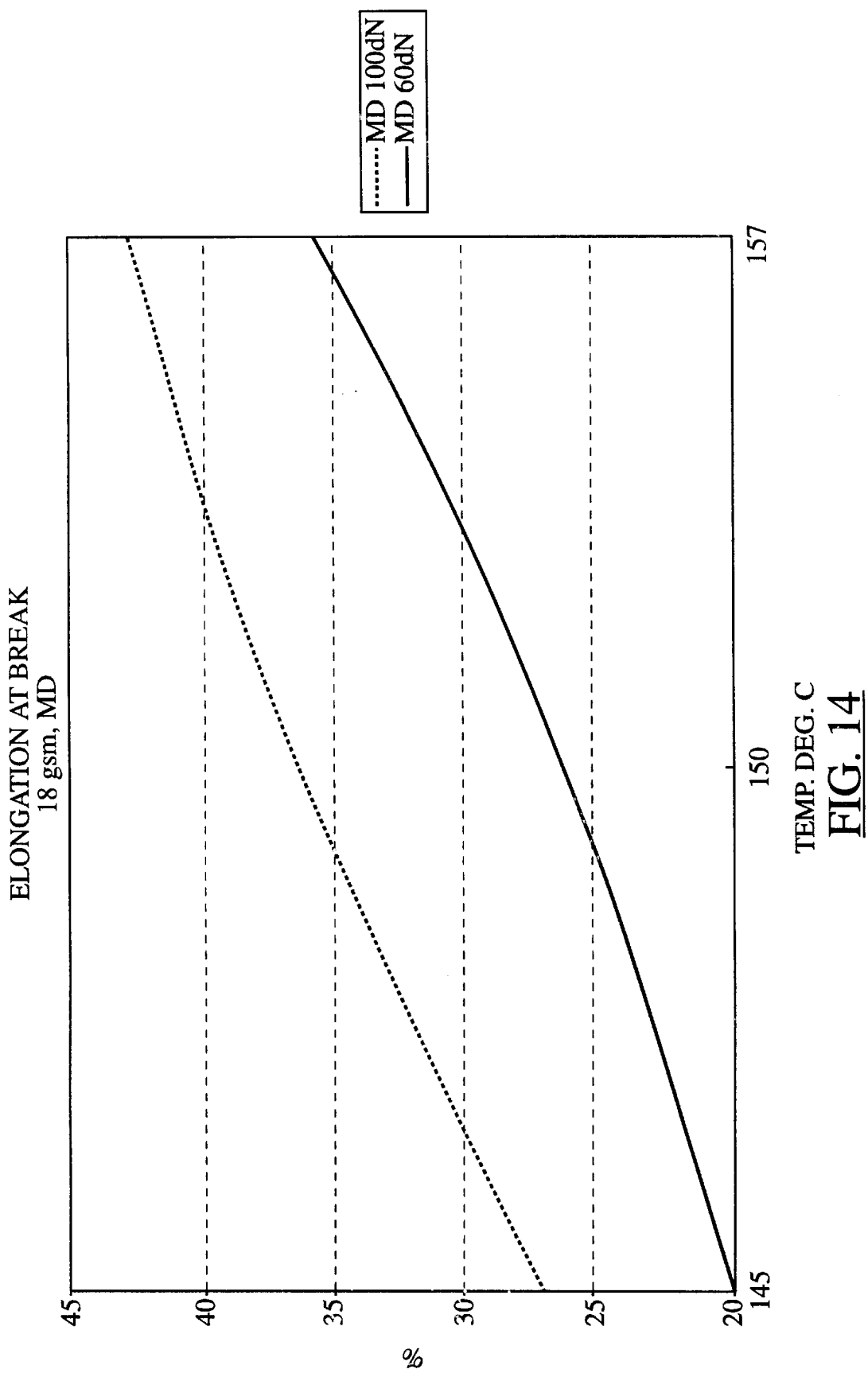
Figure 15:
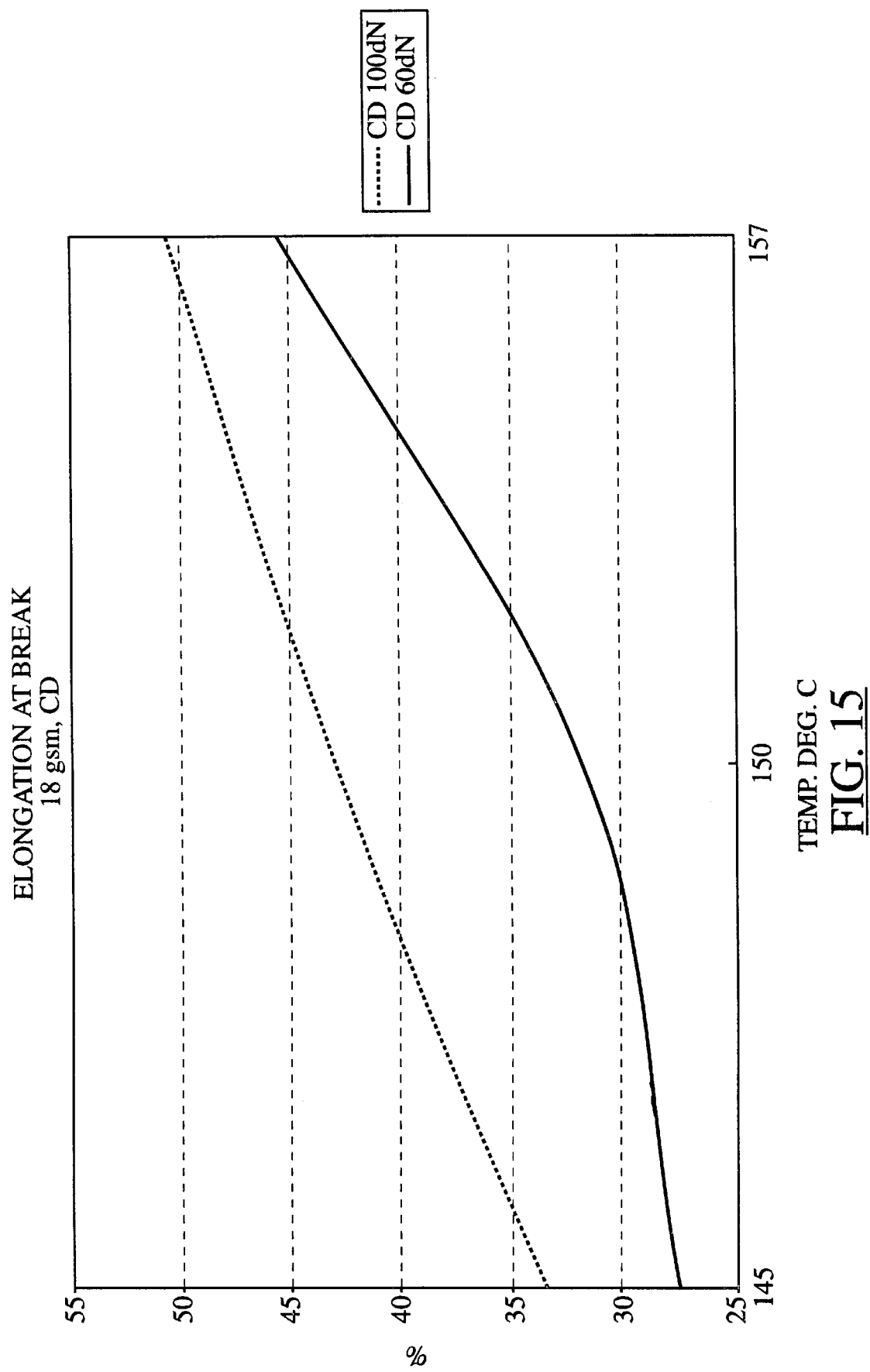

FIG. 7 schematically illustrates an exemplary process and apparatus for forming the fabrics which include hollow staple fibers. A conventional carding apparatus 60 forms a carded web 62 onto forming screen 64. The carded wed 62 includes hollow staple fibers as described above. Hollow staple fibers formed of 100% polypropylene and/or polypropylene dominant blends can be prepared using conventional techniques used for making solid staple fibers, taking into account the different spinneret designs as described above. Carding processes are well known in the art, and generally include the steps separating clumps of staple fibers into individual fibers and forming the staple fibers into a coherent web. Although a carding process is illustrated, as will be appreciated by the skilled artisan, the nonwoven fabric of the invention which includes hollow staple fibers can be formed by any of the methods known in the art for forming a nonwoven web of staple fibers, including air laying, garnetting, and similar processes known in the art.

The carded web 62 is conveyed in the longitudinal direction as indicated in FIG. 7 to a thermal treatment station 64, illustrated in FIG. 7 as heated calender rolls 66 and 68. Here the web 62 is treated to form a plurality of thermal bonds which secure the staple fibers together to form the product of the invention. The thermally bonded calendered nonwoven fabric is then removed from the thermal treatment station 64 and wound by conventional means onto roll 70. The nonwoven fabric can be stored on roll 70 or immediately passed to end use manufacturing processes, as noted above.

The invention, and how to make and use the same, will be understood more completely from the examples which follow, which are intended to be illustrative of the invention, but not to limit the scope of the invention.

EXAMPLES

Fabric samples were prepared using four. spinnerettes to form hollow fibers. On one spinbeam (referred to as spinbeam A), two spinnerettes with 64% hole area were put in position 2 and 3. Two additional spinnerettes with 47% hole area were put in positions 2 and 3 on a spinbeam adjacent spinbeam A (spinbeam B). The polymer used was a mixture of 99% Moplen H22S from Montel and 1% of a 60% titanium dioxide masterbatch. The melt temperature was about 230° C. The calender temperature and pressure were varied according to Table 1.

Fabric properties were analyzed along the web produced in a position corresponding to the border between positions 2 and 3 to insure that only hollow fibers were in the samples (a microscope investigation confirmed only hollow fibers). The rest of the line produced solid fibers.

Samples with basis weights of 18 and 23 gsm were produced at two different calender pressures and three different calender temperatures to study the bonding behavior of the hollow fibers. One sample with a basis weight of 14 gsm was also produced. Sample fabrics were stored as rolls and sheets.

The following properties of the samples were measured: basis weight, formation, fiber diameter, linear density, percentage hollowness and mechanical properties on individual fibers before bonding (only on some of the samples), tensile strength, elongation at break, rupture energy, elongation at 10 N (50 mm width), RCST (rising column strike through) on hydrophobic web, strike through and repeated strike on hydrophilic web, wet back, repeated run off on hydrophilic web, sieve test with sea sand (on some samples).

The results are summarized in Table 1 below. A more detailed discussion of various fabrics properties also follows.

TABLE 1

| | | | | | | | | | | | | | | |
|---|---|---|---|---|---|---|---|---|---|---|---|---|---|---|
| Calendar pressure | dN | 100 | 60 | 60 | 100 | 100 | 60 | 60 | 100 | 100 | 60 | 100 | 100 | 100 |
| Calendar temperature | ° C. | 157 | 157 | 157 | 157 | 150 | 150 | 150 | 150 | 150 | 145 | 145 | 145 | 145 |
| | | Roll 1 | Roll 2 | Roll 3 | Roll 4 | Roll 5 | Roll 6 | Roll 7 | Roll 8 | Roll 9 | Roll 10 | Roll 11 | Roll 12 | Roll 13 |
| Basis Weight | g/m$^2$ | 22.2 | 23.0 | 18.0 | 17.9 | 22.7 | 22.2 | 18.3 | 17.8 | 23.0 | 23.3 | 17.7 | 18.2 | 14.0 |
| Formation | | 4 | 4 | 3 | 3 | 4 | 4.5 | 3.5 | 3 | 4 | 4 | 3 | 3 | 2.5 |
| Liquid Strike Through | s | 1.9 | 1.7 | 1.8 | 2.4 | 1.9 | 2.1 | 1.8 | 1.7 | 1.8 | 2.1 | 1.9 | 1.8 | 2.1 |
| Wet Back | g | 0.1 | 0.1 | 0.1 | 0.1 | 0.1 | 0.1 | 0.2 | 0.1 | 0.1 | 0.1 | 0.2 | 0.2 | 0.5 |
| RCST | mm | 78 | 71 | 67 | 59 | 69 | 71 | 69 | 64 | 71 | 66 | 65 | 65 | 47 |
| Repeated Strike Through | 1st | 2.2 | 2.2 | 2.0 | 2.3 | 2.5 | 2.7 | 2.0 | 2.0 | 2.0 | 2.5 | 2.3 | 2.5 | 2.7 |
| | 2nd | 5.5 | 4.4 | 5.6 | 3.9 | 5.1 | 5.0 | 4.9 | 5.9 | 5.8 | 6.5 | 4.7 | 4.6 | 4.5 |
| | 3rd | 6.4 | 9.5 | 6.1 | 6.0 | 8.3 | 10.7 | 6.7 | 9.6 | 9.8 | 10.2 | 5.1 | 5.6 | 5.5 |
| Repeated Runoff | 1st | 0 | 0 | 0 | 0 | 0 | 0 | 0 | 0 | 0 | 0 | 0 | 0 | 0 |
| | 2nd | 7.1 | 8.7 | 10.8 | 12.1 | 9.8 | 9.5 | 14.3 | 13.8 | 12.9 | 12.1 | 8.2 | 9.1 | 10.2 |
| | 3rd | 19.8 | 21.5 | 21.9 | 21.4 | 21.4 | 21.4 | 20.5 | 22.5 | 21.1 | 21.5 | 20.1 | 20.3 | 23.2 |
| Tensile strength, MD | N/50 mm | 50 | 49 | 36 | 43 | 47 | 31 | 29 | 36 | 35 | 26 | 22 | 28 | 25 |
| Tensile strength, CD | N/50 mm | 32 | 25 | 36 | 22 | 24 | 17 | 12 | 17 | 18 | 14 | 10 | 14 | 9 |
| Elongation at break, MD | % | 47 | 42 | 36 | 43 | 37 | 22 | 27 | 37 | 27 | 17 | 20 | 27 | 29 |
| Elongation at break, CD | % | 56 | 43 | 46 | 51 | 38 | 28 | 32 | 43 | 30 | 23 | 27 | 34 | 39 |
| Elongation at 10 N, MD | % | 2.6 | 2.4 | 3.1 | 3.1 | 2.5 | 2.8 | 3.4 | 3.9 | 2.8 | 2.5 | 3.7 | 4.0 | 5.2 |
| Total rupture energy, MD | J | 2.61 | 2.49 | 1.65 | 2.13 | 2.13 | 1.62 | 1.44 | 1.71 | 1.62 | 1.35 | 1.14 | 1.23 | 1.05 |
| Total rupture energy, CD | J | 1.83 | 1.47 | 0.96 | 1.23 | 1.23 | 0.99 | 0.72 | 0.93 | 0.90 | 0.81 | 0.57 | 0.75 | 0.45 |
| Sieve | % | 96.1 | 96.0 | 88.8 | 90.4 | 96.5 | 96.5 | 87.3 | 89.4 | 89.9 | 96.6 | 87.6 | 86.2 | 72.3 |

| | | A-beam | B-beam | Average | | |
|---|---|---|---|---|---|---|
| Fiber diameter | micron | 20.5 | 20.2 | 20.4 | Average Apparent Linear Density | 2.65 den |
| Hollowness diameter | micron | 7.43 | 7.15 | 7.3 | Average Linear Density | 2.31 den |
| Percentage hollowness | % | 13.1 | 12.5 | 12.8 | | |

Fiber Diameter and Hollowness

The diameters of the fiber and the hollowness were measured on the web in a light microscope coupled to a computer and shown on a monitor. The measurements were not made on the cross section but from the side of the fibers. The same procedure was applied to unbonded fibers.

As the cross section of the fibers is approximately round, the outer diameter can be fairly accurately determined by this method. The cross section of the hollowness is, however, more triangular shaped than round, which means that the diameter as measured from the side depends on how the fiber is oriented when it is measured. This is also shown in the standard deviation which is much higher for the hollowness diameter than for the fiber diameter (18 and 7% respectively).

The percentage of hollowness when measured on the unbonded fibers was 19% for the A beam and 13% for the B beam. The bonded fibers, however, showed much lower hollowness (13% and 12% respectively). One possible explanation is that the heat treatment during bonding decreases the diameter of the hollowness. The fiber diameters for the bonded hollow fibers were 20.4 micron as an average. This would correspond to a denier of 2.7 if they were compact. With an average hollowness of 12% as measured on the bonded fibers, the real linear density is only 2.3.

The bonded reference fibers (without hollowness) had an average diameter of 19.4 micron, which gives a linear density of 2.4.

Properties of Single Filaments

Table 2 below summarizes the properties of unbonded samples. Two different samples from the A beam and the B beam were tested and compared to reference samples produced under similar spinning conditions, except formed of solid filaments. Also included are fibers from an earlier trial with only 6% hollowness.

refer to fabric samples described above also prepared with hollow spinnerettes at positions 2 and 3, except these samples were stored on rolls prior to evaluation. The terms "Line 1" and "Lhysa" refer to reference fabrics formed of solid filaments. The fabrics were prepared with the same raw material as the hollow samples under very similar process conditions. When producing the Lhysa samples the draw pressure in the air guns was lower than in the other cases. The calender temperature and pressure were 157° C. and 100 dN, respectively.

TABLE 2

| Fiber Strength | | B-beam | B-beam | A-beam | A-beam | Reference (Solid) | 6% hollow |
|---|---|---|---|---|---|---|---|
| Fiber diameter | (micron) | 20.2 | 20.6 | 20.2 | 19.8 | 18.5 | 19.1 |
| Linear density | (dtex) | 2.6 | 2.7 | 2.6 | 2.5 | 2.4 | 2.6 |
| % Hollowness | (%) | 13 | 13 | 19 | 19 | — | 6.3 |
| Apparent linear density | (dtex) | 2.9 | 3.1 | 3.1 | 3.0 | — | 2.7 |
| Tenacity | (N/dtex) | 0.016 | 0.015 | 0.016 | 0.016 | 0.020 | 0.020 |
| Elongation at break | (%) | 192 | 194 | 185 | 191 | 180 | 215 |
| Energy at break | (J) | 0.006 | 0.006 | 0.006 | 0.006 | — | |
| Modulus | (N/dtex) | 0.07 | 0.08 | 0.07 | 0.07 | — | |

The elongation at break is very similar for all the samples, which is expected as the spinning speeds are comparable. (Earlier investigations have shown a large influence of the spinning speed on the elongation at break for single fibers). The tenacity seems to be slightly lower for the hollow fibers.

Tensile Strength

FIGS. 8, 9, 10 and 11 are graphs illustrating the influence of bonding temperature and pressure on the tensile strength in machine direction (MD) and cross machine direction (CD) for the 18 and 23 gsm webs. Normal bonding conditions are p100 dN and 157° C.

Table 3 sets forth the properties of the hollow fiber webs as compared with selected reference webs. The term "jumbo sheets" refer to sheets of fabric prepared as described above with hollow spinnerettes at positions 2 and 3. The jumbo sheets were stored flat, and not in roll form. The term "2–3" refers to that portion of the jumbo sheet formed of hollow filaments, and the term "6" refers to that portion of the sheet formed of solid filaments. The terms "Roll 1" and "Roll 4"

By looking at the three jumbo sheets in position 6 and in-between at positions 2 and 3, one can see that the tensile strength is higher for the hollow fiber webs. One explanation is that the real denier is a little bit lower for the hollow fibers, giving more fibers for a given basis weight. A comparison with the samples from Line 1 also shows higher tensile for the hollow fiber webs. The denier for the normal production is, however, 2.4 compared to 2.3 for the hollow fibers, which gives about 5 more fiber for the hollow fibers compared with compact fibers at the same basis weight and linear density.

When comparing the fabric of Roll 4 (18 gsm, hollow fibers, outer fiber diameter of 20.4 micron and a linear density of 2.3 denier) with the Lhysa fabric (18 gsm non-woven with solid fibers having an outer fiber diameter of 21.3 micron and a linear density of 2.9 denier), the influence of the number of fibers on the tensile strength is apparent. The tensile strength of the hollow fiber sample is much higher.

TABLE 3

| | | Roll 1 | Line 1 | Jumbo Sheet 2-3 | Jumbo Sheet 6 | Jumbo Sheet 2-3 | Jumbo Sheet 6 | Jumbo Sheet 2-3 | Jumbo Sheet 6 | Line 1 | Lhysa | Roll 4 |
|---|---|---|---|---|---|---|---|---|---|---|---|---|
| Calender pressure | dN | 100 | 100 | 100 | 100 | 100 | 100 | 100 | 100 | 100 | 100 | 100 |
| Calender temperature | ° C. | 157 | 157 | 157 | 157 | 150 | 150 | 145 | 145 | 157 | 157 | 157 |
| Basis Weight | g/m$^2$ | 21.7 | 23.2 | 22.5 | 23.3 | 23.7 | 23.1 | 23.5 | 24.5 | 1.8 | 17.8 | 17.7 |
| Fiber diameter | (micron) | 20.3 | 19.4 | 20.3 | 19.3 | 20.3 | 19.3 | 20.3 | 19.3 | 19.4 | 21.3 | 20.3 |
| Real denier | (den) | 2.3 | 2.4 | 2.3 | 2.4 | 2.3 | 2.4 | 2.3 | 2.4 | 2.4 | 2.9 | 2.31 |
| Apparent denier | (den) | 2.6 | | 2.6 | | | | | | | | 2.6 |
| Tensile strength, MD | (N/50 mm) | 50 | 48 | 52 | 43 | 45 | 40 | 34 | 32 | 36 | 33 | 43 |
| Tensile strength, CD | (N/50 mm) | 32 | 30 | 33 | 28 | 24 | 23 | 20 | 18 | 20 | 17 | 22 |
| Elongation at break, MD | (%) | 47 | 50 | 52 | 40 | 38 | 35 | 29 | 28 | 45 | 44 | 43 |
| Elongation at break, CD | (%) | 56 | 54 | 52 | 41 | 37 | 37 | 29 | 29 | 51 | 53 | 51 |
| Elongation at 10 N, MD | (%) | 2.6 | | 4.1 | 4.3 | 3.8 | 4.3 | 4.2 | 4.7 | 5.5 | 5.6 | 3.1 |
| Elongation at 10 N, CD | (%) | 10.4 | | 8.2 | 9.3 | 9.4 | 10.2 | 8.9 | 10.4 | — | — | 15.3 |
| Rupture energy, MD | (J) | 2.6 | 3.7 | 2.9 | 1.9 | 2.0 | 1.7 | 1.6 | 1.4 | | 1.6 | 2.1 |
| Rupture energy, CD | (J) | 1.8 | — | 1.9 | 1.3 | 1.2 | 1.1 | 1.0 | 0.8 | | 1.0 | 1.2 |
| RCST | (mm) | 74 | | 61 | 73 | 60 | 70 | 71 | 68 | | | 59 |
| Sieve/test | Favor | 96.1 | | | 96.1* | | | | | 90 | 85.4 | 90.4 |
| | Sea Sand | 55 | | | 54 | | | | | | 14.7 | 28 |

*pos 7

Elongation at Break

FIGS. 12, 13, 14 and 15 are graphs illustrating the influence of bonding temperature and pressure on the elongation at break in MD and CD for 18 and 23 gsm webs. The elongation at break increases with bonding temperature and pressure up to the standard temperature and pressure (100 dN and 157° C.). The comparison with the Line 1 and Lhysa reference fabrics described above shows no real difference in elongation at break between the different samples. It is interesting to note the higher sensitivity of the bonding temperature on both the tensile strength and elongation at break for the hollow fibers compared to the solid fiber fabrics.

Elonqation at 10 N (50 mm strip)

Figure 16:
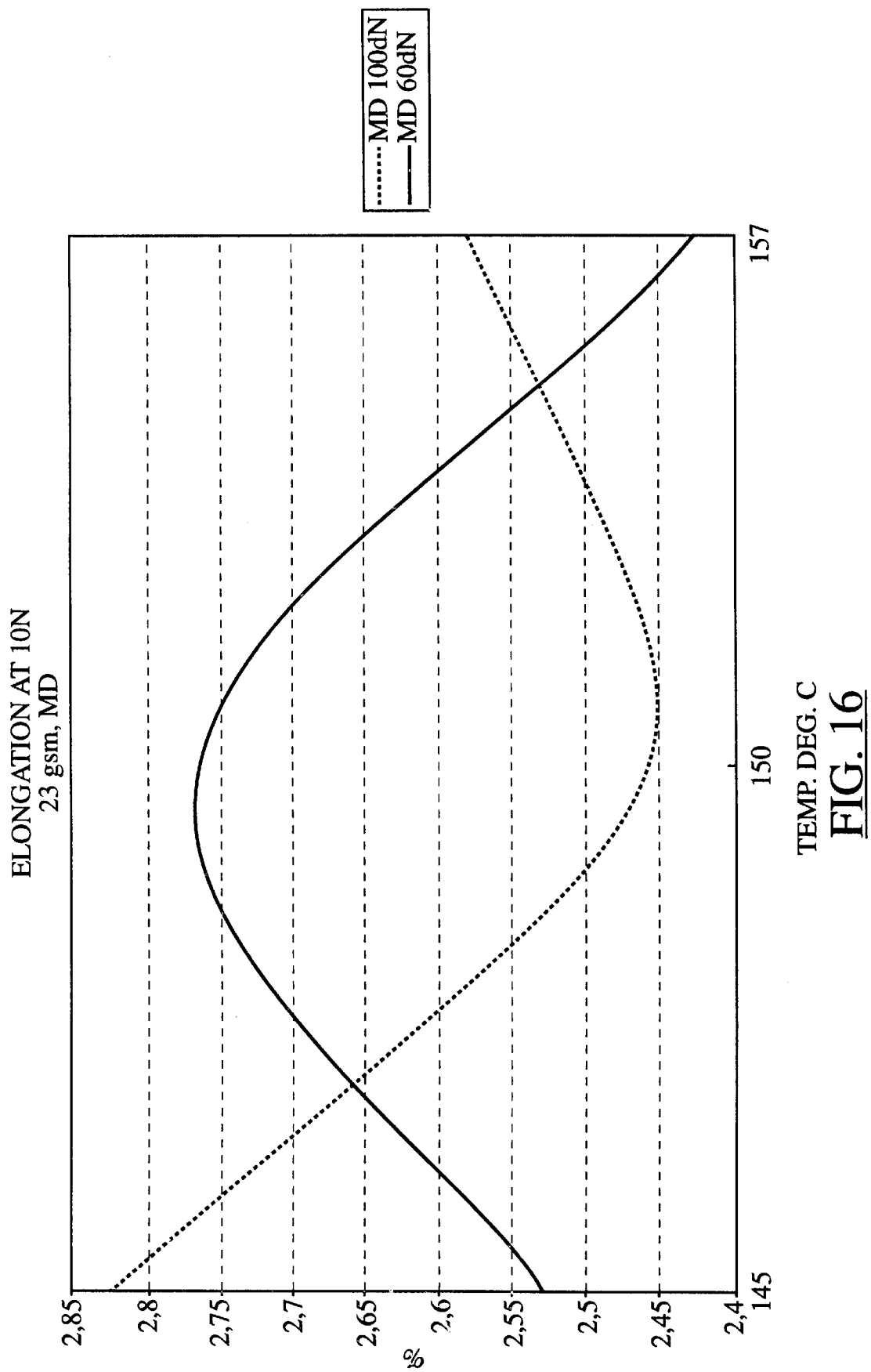
FIGS. 16 and 17 are graphs illustrating the influence of bonding temperature and pressure on elongation at 10 Newtons (N) of exemplary fabrics of the invention.
Figure 17:
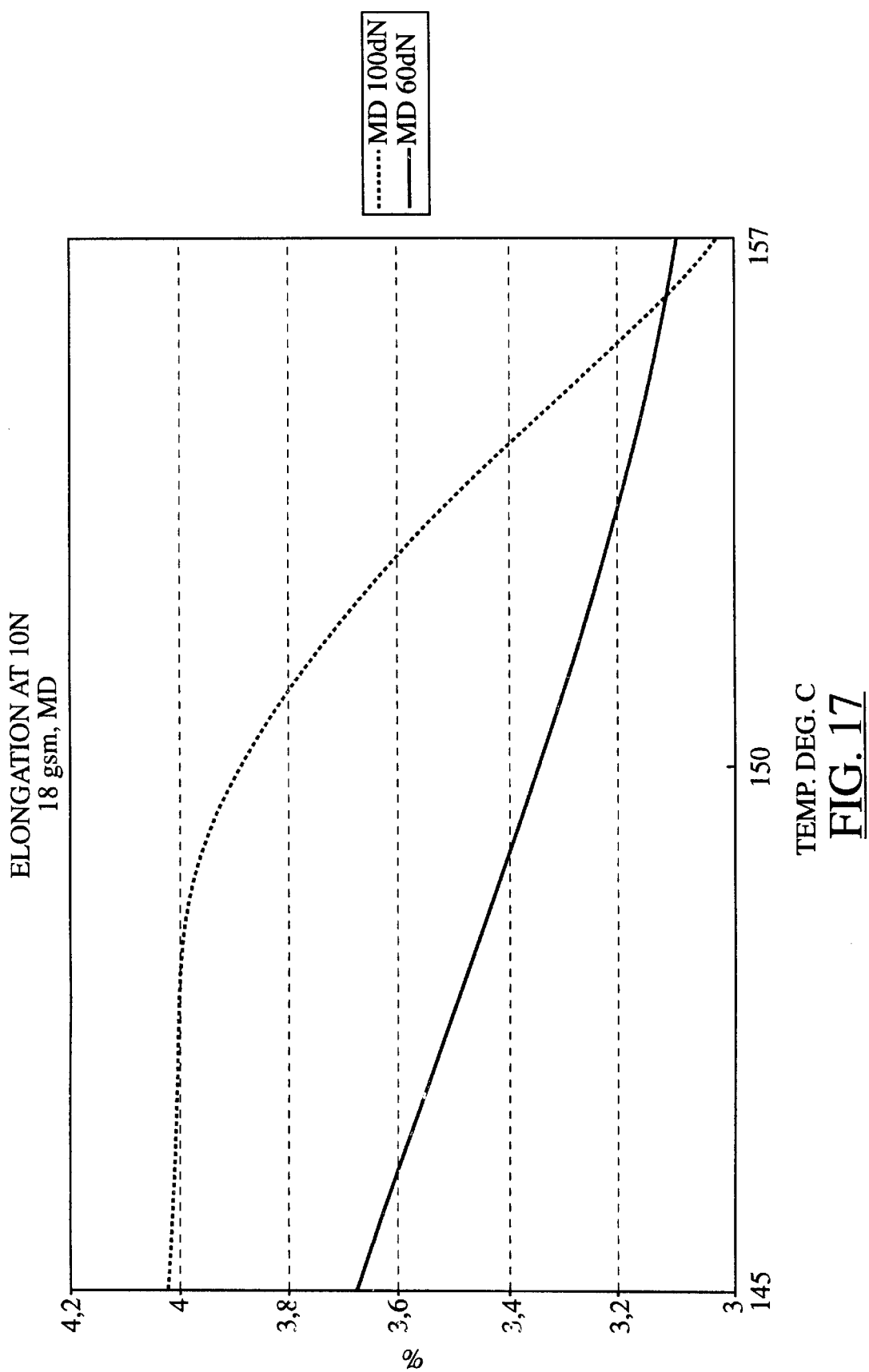

The influence of bonding temperature and pressure on elongation at 10 N is shown in FIGS. 16 and 17. The comparison of Rolls 1 and 4, formed of hollow filaments as described above, with reference fabric of Line 1 of solid filaments also as described above (23 and 18 gsm respectively) showed much lower values for the nonwoven based on hollow fibers (see Table 3). This indicates that the hollow filament fabrics may provide improved convertability, for example, in the production of diapers and the like. The measurements on the three jumbo sheets for three different bonding temperatures did, however, only show a small difference which can probably be explained by the larger number of filaments (lower liner density). One possible explanation is the sample rolls with hollow fibers were stored more than one month before tested. Due to the tension in the roll a reorientation and possibly also a recrystallisation takes place giving a stiffer material in the MD. The reference samples from Line 1 are usually tested immediately after production. As the jumbo sheets were not stored under tension, the reorientation does not take place, which can give higher elongation at 10 N in the MD for the jumbo sheet compared to the roll after storage. A support for this theory is the fact that in the CD the elongation at 10 N is higher for Roll 1 compared to the jumbo sheets.

Wet Properties

The strike through, wet back, repeated strike and repeated run off are normal for the nonwoven with hollow fibers. The webs were treated with 0.3% Silwset 12037 and evaluated.

Sieve Test

The influence of bonding temperature and pressure on permeability is shown in FIGS. 18 and 19. A comparison of the 18 gsm sample of hollow fibers (Roll 4) with reference sample from Line 1 gives the same sieve test values. This can be explained because the linear density and thus the number of fibers is roughly the same for these samples.

The same result is seen with the 23 gsm samples comparing the fabrics of Roll 1 with the reference formed of solid fibers produced at the same time (23 gsm). In this case, tests were also made with sea sand, and these values were also the same. By comparing the fabric of Roll 4 with the Lhysa sample described above, the influence of the number of fibers is nonobvious, in that the sieve test is much lower form Lhysa.

The invention has been described in considerable detail with reference to its preferred embodiments. However, it will be apparent that numerous variations and modifications can be made without departure from the spirit and scope of the invention as described in the foregoing specification and defined in the appended claims.

That which is claimed is:

1. A nonwoven fabric suitable for hygiene applications, said fabric having a basis weight ranging from about 5 to about 35 grams per square meter (gsm) and comprising a plurality of randomly arranged substantially continuous hollow filaments having an average filament diameter of about 20 microns or less and comprising a polypropylene dominant composition, wherein said filaments are thermally fused to form a coherent fabric.

2. The fabric of claim 1, wherein said hollow filaments have a hollowness of about 5% to about 70% in the cross-section of said filaments.

3. The fabric of claim 2, wherein said hollow filaments have a hollowness of about 10% to about 50% in the cross-section of said filaments.

4. The fabric of claim 1, wherein said hollow filaments are formed of a 100 percent polypropylene composition.

5. The fabric of claim 1, wherein said hollow filaments are formed of a polypropylene dominant composition comprising greater than 50 percent by weight polypropylene and less than 50 percent by weight of at least one other polymer.

6. The fabric of claim 5, wherein said at least one other polymer is polyethylene.

7. The fabric of claim 1, wherein said fabric comprises discrete bond sites comprising thermal point bonds wherein the filaments are fusion bonded to one another and wherein the hollow filaments are collapsed.

8. A nonwoven fabric suitable for hygiene applications, said fabric having a basis weight ranging from about 5 to about 35 grams per square meter (gsm) and comprising a plurality of randomly arranged hollow staple fibers having an average fiber diameter of about 20 microns or less and comprising a polypropylene dominant composition, wherein said fibers are thermally fused to form a coherent fabric.

9. The fabric of claim 8, wherein said hollow staple fibers have a hollowness of about 5% to about 70% in the cross-section of said fibers.

10. The fabric of claim 9, wherein said hollow staple fibers have a hollowness of about 10% to about 50% in the cross-section of said fibers.

11. The fabric of claim 8, wherein said hollow staple fibers are formed of a 100 percent polypropylene composition.

12. The fabric of claim 8, wherein said hollow staple fibers are formed of a polypropylene dominant composition comprising greater than 50 percent by weight polypropylene and less than 50 percent by weight of at least one other polymer.

13. The fabric of claim 12, wherein said at least one other polymer is polyethylene.

14. The fabric of claim 8, wherein said fabric comprises discrete bond sites comprising thermal point bonds wherein the fibers are fusion bonded to one another and wherein the hollow fibers are collapsed.

15. The fabric of claim 8, wherein said fabric is a carded fabric.

16. A disposable absorbent article comprising a nonwoven spunbonded fabric component suitable for hygiene applications, said nonwoven spunbonded fabric component having a basis weight ranging from about 5 to about 35 grams per square meter (gsm) and at least one other component, said nonwoven spunbonded fabric component comprising a plurality of randomly deposited substantially continuous hollow filaments having an average filament diameter of about 20 microns or less and comprising a polypropylene dominant composition, wherein said filaments are thermally fused to form a coherent fabric.

17. A disposable absorbent article comprising a nonwoven fabric component suitable for hygiene applications, said nonwoven fabric component having a basis weight ranging from about 5 to about 35 grams per square meter (gsm) and at least one other component, said nonwoven fabric component comprising a plurality of randomly deposited hollow staple fibers having an average fiber diameter of about 20 microns or less and comprising a polypropylene dominant composition, wherein said fibers are thermally fused to form a coherent fabric.

18. The disposable absorbent article of claim 16, wherein said substantially continuous hollow filaments are formed of a 100 percent polypropylene composition.

19. The disposable absorbent article of claim 18, wherein said 100 percent polypropylene composition comprises isotactic polypropylene.

20. The disposable absorbent article of claim 16, wherein said substantially continuous hollow filaments are formed of a polypropylene dominant composition comprising greater than 50 percent by weight polypropylene and less than 50 percent by weight of at least one other polymer.

21. The disposable absorbent article of claim 20, wherein said at least one other polymer is polyethylene.

22. The disposable absorbent article of claim 17, wherein said hollow staple fibers are formed of a 100 percent polypropylene composition.

23. The disposable absorbent article of claim 22, wherein said 100 percent polypropylene composition comprises isotactic polypropylene.

24. The disposable absorbent article of claim 17, wherein said hollow staple fibers are formed of a polypropylene dominant composition comprising greater than 50 percent by weight polypropylene and less than 50 percent by weight of at least one other polymer.

25. The disposable absorbent article of claim 24, wherein said at least one other polymer is polyethylene.

26. The fabric of claim 4, wherein said 100 percent polypropylene composition comprises isotactic polypropylene.

27. The fabric of claim 6, wherein said polypropylene composition comprises from about 2 to about 20 percent by weight polyethylene and from about 80 to about 98 percent by weight polypropylene.

28. The fabric of claim 11, wherein said 100 percent polypropylene composition comprises isotactic polypropylene.

29. The fabric of claim 13, wherein said polypropylene composition comprises from about 2 to about 20 percent by weight polyethylene and from about 80 to about 98 percent by weight polypropylene.

30. The disposable article of claim 21, wherein said polypropylene composition comprises from about 2 to about 20 percent by weight polyethylene and from about 80 to about 98 percent by weight polypropylene.

31. The disposable article of claim 25, wherein said polypropylene composition comprises from about 2 to about 20 percent by weight polyethylene and from about 80 to about 98 percent by weight polypropylene.

* * * * *

UNITED STATES PATENT AND TRADEMARK OFFICE
CERTIFICATE OF CORRECTION

PATENT NO. : 6,368,990 B1
DATED : April 9, 2002
INVENTOR(S) : Jennergren et al.

It is certified that error appears in the above-identified patent and that said Letters Patent is hereby corrected as shown below:

Title page,
Item [60], Related U.S. Application Data, "Aug. 5, 1997" should read
-- Aug. 4, 1997 --.
Item [56], References Cited, OTHER PUBLICATIONS,
"Absracts" should read -- Abstracts --.

Column 1,
Line 8, "Aug. 5, 1997" should read -- Aug. 4, 1997 --.

Signed and Sealed this

Twenty-fourth Day of September, 2002

Attest:

Attesting Officer

JAMES E. ROGAN
*Director of the United States Patent and Trademark Office*